(12) United States Patent
O'Lenick, Jr.

(10) Patent No.: US 7,049,476 B1
(45) Date of Patent: May 23, 2006

(54) GUERBET POLYMERS

(75) Inventor: Anthony J. O'Lenick, Jr., Dacula, GA (US)

(73) Assignee: SurfaTech Coprporation, Dacula, GA (US)

( * ) Notice: Subject to any disclaimer, the term of this patent is extended or adjusted under 35 U.S.C. 154(b) by 28 days.

(21) Appl. No.: 11/015,896

(22) Filed: Dec. 20, 2004

(51) Int. Cl.
*C07C 31/24* (2006.01)
*C07C 31/18* (2006.01)

(52) U.S. Cl. ........................ 568/852; 528/425
(58) Field of Classification Search ............... 568/852; 528/425
See application file for complete search history.

(56) References Cited

U.S. PATENT DOCUMENTS 5,488,121 A * 1/1996 O'Lenick, Jr. .............. 554/167

* cited by examiner

*Primary Examiner*—Elvis O. Price

(57) ABSTRACT

The present invention is drawn to a series of highly branched, essentially saturated, liquid oil phases having primary alcohol groups, and a method of treating skin. The polymers of the present invention are high molecular weight oil phases which provide outstanding lubrication and conditioning to skin.

17 Claims, No Drawings

GUERBET POLYMERS

FIELD OF THE INVENTION

The present invention is drawn to a series of highly branched, essentially saturated, liquid oil phases having primary alcohol groups, and a method of treating skin. The polymers of the present invention are high molecular weight oil phases which provide outstanding lubrication and conditioning to skin.

BACKGROUND OF THE INVENTION

Guerbet alcohols have been known for over 100 years now. Marcel Guerbet pioneered the basic chemistry in the 1890s. It has allowed for the synthesis of a regiospecific beta branched hydrophobe which introduces high purity, branching into the molecule.

Guerbet alcohols have been known since the 1890's when Marcel Guerbet first synthesized these materials. The reaction sequence, which bears his name, is related to the Aldol Reaction and occurs at high temperatures under catalytic conditions. The overall reaction can be represented by the following equation;

The product is an alcohol with twice the molecular weight of the reactant alcohol minus a mole of water. The reaction proceeds by a number of sequential steps. These steps including (a) oxidation of alcohol to aldehyde, (b) aldol condensation after proton extraction, (c) dehydration of the Aldol product, (d) hydrogenation of the allylic aldehyde.

The reaction takes place without catalyst, but it is strongly catalyzed by addition of hydrogen transfer catalysts. At low temperatures 130–140° C. the rate-limiting step is the oxidation process (i.e. formation of the aldehyde). At somewhat higher temperatures 160–180° C. the rate-limiting step is the Aldol Condensation. At even higher temperatures other degradative reactions occur and can become dominant.

Many catalysts have been described in the literature as effective for the preparation of Guerbet Alcohols. These catalysts, hereafter referred to as Guerbet catalysts, include, nickel, lead salts (U.S. Pat. No. 3,119,880), oxides of copper, lead, zinc, chromium, molybdenum, tungsten, and manganese (U.S. Pat. No. 3,558,716), palladium compounds and silver compounds, and many others U.S. Pat. No. 3,979,466 and U.S. Pat. No. 3,864,407), and mixtures thereof. All patents are incorporate herein by reference.

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the Guerbet process gives essentially 100% product.

As should be apparent from the above reaction, the Guerbet reaction takes two moles of a primary alcohol and condenses them to make a regiospecific beta branched primary alcohol of twice the molecular weight. The present invention surprisingly makes use of this reaction sequence, but on a diol, in which the reaction occurs on both sides of the molecule. This results in a polymerization reaction increasing molecular weight, introducing beta branching and doubling the molecular weight. The reaction proceeds with the diol until the mono substituted alcohol reacts and caps the sequence. By modification of the ratio of capper to diol the molecular weight is controlled. As the concentration of capper increases the molecular weight decreases.

Guerbet alcohols have unusual properties. These unique properties are partly attributed to their high molecular weight and high level of saturation (A. J. O'Lenick Jr. and R. E. Bilbo, Soap/Cosmetics/Chemical Specialties, April 1987, page 52). Unusual properties are attributed to the so called "beta branch point". Some of the properties attributed to Guerbet alcohols are low irritation, liquidity to extremely low temperatures, low volatility, relatively reactive and easy to derivitize, useful superfatting agents to re-oil the skin and hair, highly lipophilic, good oxidation stability, and excellent color stability.

U.S. Pat. No. 4,425,458 issued in 1984 to Lindner et al teaches that certain Guerbet alcohol diesters are useful as plastic lubricants.

U.S. Pat. No. 4,731,190 issued in 1988 and U.S. Pat. No. 4,830,769 both issued to O'Lenick et al, and incorporated herein by reference, teaches that certain Guerbet alcohol alkoxylates are useful as metal working lubricants.

U.S. Pat. No. 4,868,236 issued in 1989 to O'Lenick teaches that certain Guerbet alcohol citrate esters are useful as plastic lubricants.

U.S. Pat. No. 4,800,077 issued in 1989 to O'Lenick et al, which is incorporated herein by reference, teaches that certain Guerbet alcohol based quaternary compounds are useful liquid cosmetic and personal care compounds.

U.S. Pat. No. 5,488,121 to O'Lenick, incorporated herein by reference, discloses di-guerbet esters based upon the reaction product of both a Guerbet acid and a Guerbet alcohol.

U.S. Pat. No. 5,786,389 issued in 1998 to O'Lenick et al, incorporated herein by reference, teaches that certain castor esters made by the reaction of a Guerbet alcohol and castor oil provide gloss to the skin.

Despite the considerable patenting of products based upon Guerbet alcohol technology, it was not until the present invention that the Guerbet reaction sequence has been utilized to produce polymeric materials by the reaction of a diol, which functions as a chain extender, and a fatty alcohol that functions as a chain terminator. The reaction provides highly branched, oxidatively stable, oil phases with many hydroxyl groups.

The compounds of the present invention are outstanding lubricating oils, and also find application in the cosmetic arts as superfatting materials. They replenish oils into the skin when applied topically. Another key use for the compounds of the present invention is as raw materials for preparation of esters.

THE INVENTION

SUMMARY OF THE INVENTION

The present invention is directed to a series of polymeric products that are highly branched in a very regiospecific way. The branching pattern is beta and a primary alcohol is presenting the molecule. The molecules have very low iodine values and consequently are both liquid and oxidatively stable. They are low in viscosity for a given molecular weight when compared to the linear compounds having the same number of carbon atoms.

The molecular weight of the molecule is controlled by the amount of capper used in the reaction. The capper is a mono-functional alcohol that does not polymerize. The result is a polymer that can be customized in terms of molecular weight. The ability to control the molecular weight also controls the functional properties of the polymer. The higher molecular weight polymers have a higher viscosity and are more lubricous. The lower molecular weight products have a dryer feel on the skin.

In addition to controlling the molecular weight of the polymer, the molecular weight of the capper also plays a role. The higher the molecular weight of the capper the higher the melt point of the polymer.

OBJECTIVE OF THE INVENTION

One of the objectives of the current invention is to provide a series of polymers that are not based upon free radical chemistry that can be customized for specific applications. Unlike free radical polymers which use vinyl compounds as reactants, the polymers of the present invention are vinyl free. Vinyl materials are not desirable in personal care applications.

Another objective of the invention is the use of the polymers of the present invention as lubricating oils in the metal working and other industries. The superior oxidative stability, lubrication properties and ability to control molecular weight make these materials unique in this application.

Another objective of the present invention is the use of the polymers of the present invention as additives for skin care in the personal care market. They are mild, that is well tolerated by skin and eyes, and provides a very pleasant feel on the skin. They replace the oils in the skin, keeping them soft and comfortable.

Other objectives of the invention will become apparent as one reads the current application.

DETAILED DESCRIPTION OF THE INVENTION

One aspect of the present invention relates to a Guerbet polymer which conforms to the following structure:

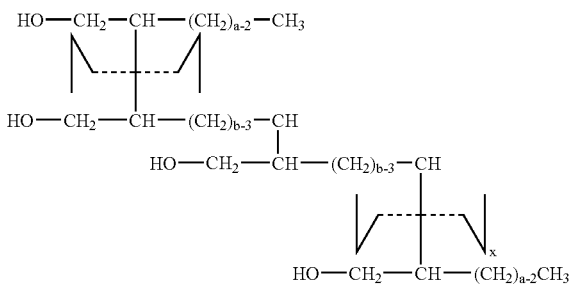

wherein;

a is an integer ranging from 7 to 21;

b is an integer ranging from 8 to 12;

x is an integer ranging from 1 to 500.

Another aspect of the invention relates to Guerbet polymer prepared by the reaction of (A) a monofunctional fatty alcohol conforming to the following structure:

a is an integer ranging from 7 to 21;

with (B) a diol conforming to the following structure:

b is an integer ranging from 8 to 12;

wherein said reaction is conducted at a temperature of between 180° C. and 250° C., in the presence of a Guerbet reaction catalyst.

Still another aspect of the present invention is a process for conditioning skin which comprises contacting the skin with an effective conditioning concentration of a polymeric Guerbet which conforms to the following structure:

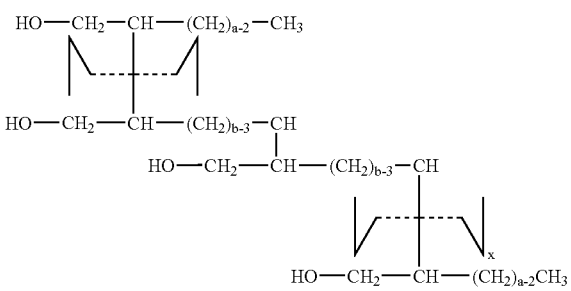

wherein;

a is an integer ranging from 7 to 21;

b is an integer ranging from 8 to 12;

x is an integer ranging from 1 to 500.

PREFERRED EMBODIMENTS

In a preferred embodiment b is 8.
In a preferred embodiment b is 10.
In a preferred embodiment b is 12.
In a preferred embodiment a is 7.
In a preferred embodiment a is 9.
In a preferred embodiment a is 17.
In a preferred embodiment a is 21.
In a preferred embodiment the Guerbet reaction catalyst is ZnO.
In a preferred embodiment the effective conditioning concentration ranges from 0.1 to 25% by weight.

EXAMPLES

Reactants

Fatty Alcohol (Capper)

a is an integer ranging from 7 to 21.

Fatty alcohols are commercially available from a variety of sources including Sassol (formerly Condea).

| Example | a Value | common name |
|---------|---------|-------------|
| 1 | 7 | capryl alcohol |
| 2 | 9 | decyl alcohol |
| 3 | 11 | lauryl alcohol |
| 4 | 13 | myristyl alcohol |
| 5 | 15 | palmityl alcohol |
| 6 | 17 | stearyl alcohol |
| 7 | 19 | aracadinyl alcohol |
| 8 | 21 | behenyl alcohol |

Diol (Chain Extender)

Diol alcohols are commercially available from a variety of sources including Jarchem Industries Inc. 414 Wilson Avenue Newark, N.J. 07105. They conform to the following structure:

$$HO-(CH_2)_b-OH$$

b is an integer ranging from 8 to 12.

| Example | b Value |
|---------|---------|
| 9 | 8 |
| 10 | 10 |
| 11 | 12 |

Product

Polymeric Guerbet Alcohol

The reaction sequence used to make the products of the current invention are as follows;

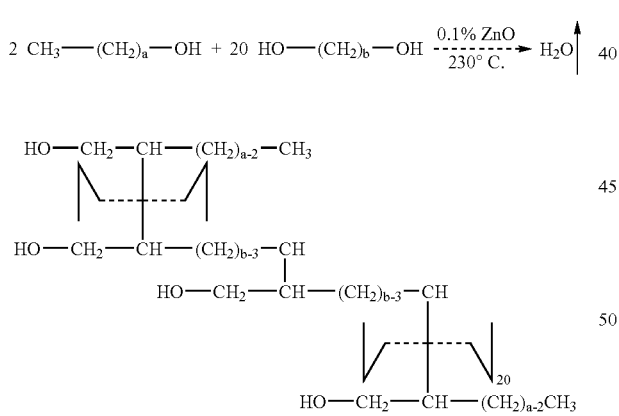

General Procedure

To the a clean dry reaction flask equipped with heating, thermometer, agitation, vacuum and an ability to remove water is added the specified number of grams of the specified chain capper (examples 1–8). Next add the specified number of grams of the specified diol (example 9–11). Next add 0.1% by weight, based upon the total weight of the capper and diol of ZnO. Mix well and heat to 230° C. The reaction will begin at about 170° C. The heating should be rapid, most commonly with 1–2 hours. The reaction progress is monitored by water generated and a drop in hydroxyl value. When the hydroxyl value approaches theoretical, the reaction is cooled and the product filtered at 100° C. The product is used without additional purification.

| Example | Capping alcohol | | Diol | | x value |
|---------|---------|-------|---------|----------|---------|
| | Example | Grams | Example | Grams | |
| 12 | 1 | 260.0 | 9 | 146.0 | 1 |
| 13 | 2 | 316.0 | 10 | 1740.0 | 10 |
| 14 | 3 | 372.0 | 11 | 3480.0 | 20 |
| 15 | 4 | 428.0 | 9 | 5840.0 | 40 |
| 16 | 5 | 484.0 | 10 | 8700.0 | 50 |
| 17 | 6 | 540.0 | 11 | 1010.0 | 5 |
| 18 | 7 | 596.0 | 9 | 14600.0 | 100 |
| 19 | 8 | 652.0 | 10 | 3480.0 | 20 |
| 20 | 8 | 652.0 | 10 | 101000.0 | 500 |

The compounds of example 12–20 are highly lubricious and oxidatively stable. They provide an outstanding feel on the skin as prepared, when diluted in solvent, when formulated into lotions, and emulsions.

The products of the above reaction can be reacted with fatty acids to make esters.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

I claim:

1. A Guerbet polymer which conform to the following structure:

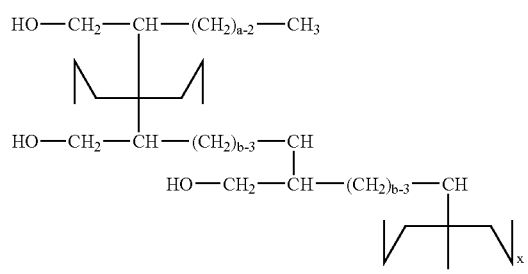

wherein;

a is an integer ranging from 7 to 18;
b is an integer ranging from 8 to 12;
x is an integer ranging from 1 to 500.

2. A polymeric Guerbet of claim 1 wherein b is 8.
3. A polymeric Guerbet of claim 1 wherein b is 10.
4. A polymeric Guerbet of claim 1 wherein b is 12.
5. A polymeric Guerbet of claim 1 wherein a is 7.
6. A polymeric Guerbet of claim 1 wherein a is 9.
7. A polymeric Guerbet of claim 1 wherein a is 17.
8. A polymeric Guerbet of claim 1 wherein a is 21.
9. A process for conditioning skin which comprises contacting the skin with an effective conditioning concentration of a polymeric Guerbet which conforms to the following structure:

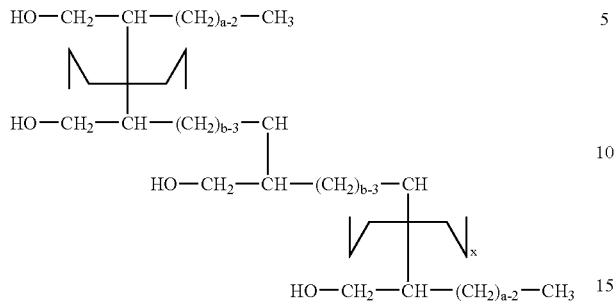

wherein;
a is an integer ranging from 7 to 18;
b is an integer ranging from 8 to 12;
x is an integer ranging from 1 to 500.

10. A process of claim 9 wherein said effective conditioning concentration ranges from 0.1 to 25% by weight.

11. A process according to claim 10 wherein b is 8.

12. A process according to claim 10 wherein b is 10.

13. A process according to claim 10 wherein b is 12.

14. A process according to claim 10 wherein a is 7.

15. A process according to claim 10 wherein a is 9.

16. A process according to claim 10 wherein a is 17.

17. A process according to claim 10 wherein a is 21.

* * * * *

UNITED STATES PATENT AND TRADEMARK OFFICE
CERTIFICATE OF CORRECTION

PATENT NO.       : 7,049,476 B1                                              Page 1 of 1
APPLICATION NO.  : 11/015896
DATED            : May 23, 2006
INVENTOR(S)      : Anthony J. O'Lenick It is certified that error appears in the above-identified patent and that said Letters Patent is hereby corrected as shown below:

In Claim 1

Delete: " 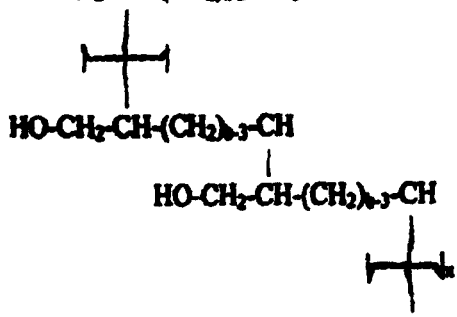 "

And insert therefore -- 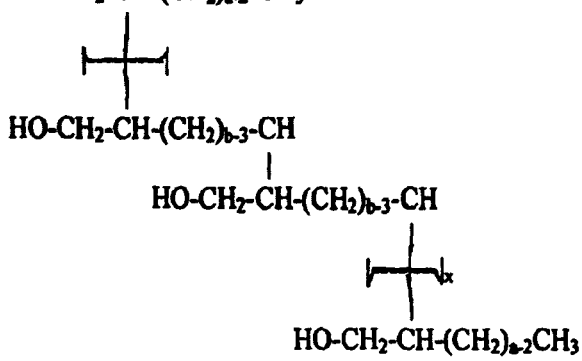 --

Signed and Sealed this

Third Day of October, 2006

JON W. DUDAS
*Director of the United States Patent and Trademark Office*